(12) United States Patent
Wesselmann et al.

(10) Patent No.: US 11,357,957 B2
(45) Date of Patent: Jun. 14, 2022

(54) METHOD AND DEVICE FOR FORMING A BALLOON (71) Applicant: BIOTRONIK AG, Buelach (CH)

(72) Inventors: Matthias Wesselmann, Ruedlingen (CH); Amir Fargahi, Buelach (CH); Christoph Hoser, Zurich (CH); Daniela Santos, Zurich (CH); Bodo Quint, Dettighofen (DE); Tobias Schaefer, Blumberg-Fuetzen (DE)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 16/769,071

(22) PCT Filed: Sep. 25, 2018

(86) PCT No.: PCT/EP2018/075882
§ 371 (c)(1),
(2) Date: Jun. 2, 2020

(87) PCT Pub. No.: WO2019/120655
PCT Pub. Date: Jun. 27, 2019

(65) Prior Publication Data
US 2020/0338323 A1 Oct. 29, 2020

(30) Foreign Application Priority Data
Dec. 19, 2017 (EP) .................................... 17208516

(51) Int. Cl.
*B29C 49/16* (2006.01)
*A61M 25/10* (2013.01)
*B29C 49/00* (2006.01)
*B29C 49/28* (2006.01)
*B29C 49/46* (2006.01)

(52) U.S. Cl.
CPC ...... *A61M 25/1029* (2013.01); *A61M 25/104* (2013.01); *B29C 49/0073* (2013.01); *B29C 49/16* (2013.01); *B29C 49/28* (2013.01); *B29C 49/46* (2013.01); *A61M 2207/10* (2013.01);
(Continued)

(58) Field of Classification Search
None
See application file for complete search history.

(56) References Cited

U.S. PATENT DOCUMENTS 5,087,394 A * 2/1992 Keith ................ A61M 25/1029
264/291
5,587,125 A * 12/1996 Roychowdhury ..........................
A61M 25/1029
264/512

(Continued)

OTHER PUBLICATIONS

Muller, Gerard, International Search Report for Application No. PCT/EP2018/075882; dated Jan. 3, 2019.
(Continued)

*Primary Examiner* — Monica A Huson
(74) *Attorney, Agent, or Firm* — Greer, Burns & Crain, Ltd.; Steven P. Fallon (57) ABSTRACT

A method for forming a balloon provides a preform that encloses an internal space. The preform is pre-heated to a shaping temperature by passing a heated gas or fluid via an inlet of the preform into the internal space. The preform is then shaped the preform into a balloon. A device is configured to heat a preform using heated gas or fluid to decouple heating from the temperature of a shaping tool.

20 Claims, 3 Drawing Sheets

(52) U.S. Cl.
CPC ............. *B29C 2049/0089* (2013.01); *B29C 2049/4638* (2013.01)

(56) References Cited

U.S. PATENT DOCUMENTS

| | | |
|---|---|---|
| 6,863,856 B1 | 3/2005 | Mahoney et al. |
| 8,043,553 B1 * | 10/2011 | Durcan ............. B29C 55/24 |
| | | 264/573 |
| 2014/0114394 A1 | 4/2014 | Gale et al. |
| 2017/0100265 A1 | 4/2017 | Bar et al. |

OTHER PUBLICATIONS

Muller, Gerard, European Search Report for Application No. EP 17208516.9; dated Jul. 5, 2018.

* cited by examiner

METHOD AND DEVICE FOR FORMING A BALLOON

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2018/075882, which was filed Sep. 25, 2018, which application claimed priority from European Application EP17208516.9, which was filed Dec. 19, 2017.

FIELD OF THE INVENTION

A field of the invention is the manufacture of balloons for balloon catheters.

BACKGROUND

Angioplasty, also denoted as transluminal angioplasty, is a procedure for widening or re-opening constricted or closed blood vessels, particularly via balloon dilation.

Such balloons are placed into the stenosis/constriction with a catheter, particularly using a guide wire, wherein the balloon is arranged at a distal end region of the catheter. Here, distal defines that the region is remote from the user/physician handling the catheter. Accordingly, proximal refers to regions closer to the user/physician along the catheter.

To widen the constriction, the balloon is inflated (e.g. with a pressure in the range from 7 bar to 30 bar) in the constricted area of the blood vessel by filling it with a pressurized fluid.

Due to the expanding balloon, the constricted vessel area is widened or re-opened again. Additionally, a support structure such as a stent can be implanted by the balloon in the former constricted area.

Usually, for forming an angioplasty balloon, the following steps are carried out: softening of a preform by heating the preform to a shaping temperature via heat exchange with the tool or IR heaters by heat conduction and/or radiation,
  shaping the preform to a balloon by stretch blow molding of the preform under tension and internal pressure in a stretch blow molding tool
  annealing the balloon in the tool under pressure at an annealing temperature above the glass transition temperature of the preform material and below the melting temperature of the perform material
  cooling the balloon below the glass transition temperature.

In such forming processes the shaping temperature of the preform (e.g. balloon tube) can only be tightly controlled when the tool temperature is at the same level as the shaping temperature. This depends on blow velocity and the temperature gradient between the preform and the molding tool. However, a heating of the preform material still occurs, while the preform stretches, if the molding tool is set at a higher temperature than the chosen preform shaping temperature. A temperature deviation from the shaping temperature can occur, which softens the preform material and increases the axial elongation of the preform under tension more than desired. Such temperature deviation can therefore limit the achievable wall thickness of the balloon formed from this preform.

In this regard it is desirable to have a process for forming a balloon for a balloon catheter in which the shaping temperature can be quickly reached and in which the actual preform temperature deviates as little as possible from the pre-defined shaping temperature.

SUMMARY OF THE INVENTION

A preferred method for forming a balloon includes providing a (e.g. elongated) preform having a circumferential wall that encloses an internal space of the preform, pre-heating the preform to a shaping temperature by passing a heated gas or fluid via an inlet of the preform into the internal space (particularly so that heat of the gas or fluid is transferred to the inner wall of the preform), and shaping the preform into a balloon.

A preferred device for shaping a balloon includes a tool configured to receive a preform that is to be shaped into a balloon. The device has at least a first clamping device to hold a first end section of the preform when the preform is arranged in the tool. At least a first heater is configured to heat a gas or a fluid. The first heater is in fluid connection with the first clamping device such that a gas or fluid heated by the first heater can be passed into an internal space of the preform via an inlet of the preform at the first end section of the preform.

BRIEF DESCRIPTION OF THE DRAWINGS

In the following, embodiments and further features of the present invention are described with reference to the Figures, wherein.

DETAILED DESCRIPTION OF THE PREFERRED EMBODIMENTS

Preferred methods and devices enable balloon or preform material to be reproducibly heated from room temperature to the shaping temperature in a fast and precise manner, even for varying preform (e.g. balloon tube) cross sections. Particularly, advantageously, this balloon material/preform pre-heating is decoupled from the temperature of the tool.

Preferably, according to an embodiment of the present invention, the gas used for pre-heating/shaping of the preform is air, but other gases may also be used, particularly inert gases such as nitrogen or moist air.

Particularly, in an embodiment, upon heating, the gas or fluid can exit the preform via an outlet of the preform, which outlet opposes the inlet, so that a continuous flow of heated gas or fluid is passed through the preform for heating the latter.

Furthermore, according to an embodiment of the method according to the present invention, the step of providing the preform corresponds to providing a tool having a tube extending in an axial direction, a first and an opposing second cone facing each other in the axial direction, and arranging the preform in the tool, such that the preform extends in the axial direction through the first cone, the tube and the second cone and is surrounded by the first cone, the tube and the second cone.

Preferably, the cones are formed out of a metal or high temperature thermoplastic, while the tube is preferably formed out of a glass or metal.

Preferably, the cones and the tube define the form of the balloon to be formed and delimit the dimension of the balloon in the axial direction and in the radial direction (the respective radial direction extends perpendicular to the axial direction).

Preferably, upon shaping, the preform can be (plastically) expanded until it contacts a tapered inside of the first cone as well as a tapered inside of the second cone as well as the circumferential, preferably cylindrical, inside of the tube.

Preferably, pre-heating takes place in a so-called axial phase, radial phase and final phase, which phases may also be partially superimposed.

Preferably, in the axial phase, the heated gas or fluid travels as an axial heating wave through the initially cold preform and gradually cools down by transferring heat to the inner surface of the preform (e.g. balloon tube).

When the inner surface temperature of the preform gets close to the temperature of the heated gas or fluid (e.g. to a few degrees), the heat transfer from the heated gas or fluid to the inner preform surface drops. At this time the axial temperature profile is almost homogenous and a second temperature wave travels in the radial direction through the preform material due to heat conduction.

In the final phase, the final temperature profile is established due to radiant heat exchange and thermal conduction with the surroundings.

Furthermore, according to an embodiment of the method according to the present invention, a first end section of the preform having the inlet is held by a first clamping device such that the heated gas or fluid can be passed into the preform via the inlet.

Furthermore, according to an embodiment of the method according to the present invention, heating of the gas is performed outside the tool in a first heater, preferably upstream the first clamping device. Preferably, the first heater is a flow heater.

Preferably, the first heater has a power that is large enough to prevent a decrease of the temperature of the gas also when the gas has a maximal flow rate. This guarantees (without the necessity of employing additional measurement instrumentation) that the temperature differences along the preform are minimal, at least as long as the preform is purged with the heated gas or fluid. This is due to the fact that the heat transfer via the forced convection is significantly larger than the heat exchange with the ambience.

Preferably, according to an embodiment of the method according to the present invention, the first heater controls the temperature of the gas or fluid so that the heated gas or fluid has a pre-definable (e.g. constant) temperature. The control can be a closed-loop control. Alternatively, also an open-loop control may be applied.

Further, according to an embodiment of the method according to the present invention, a second end section of the preform, which second end section protrudes out of the second cone and has an outlet of the preform, is held by a second clamping device, wherein preferably the second clamping device is in an open state upon pre-heating of the pre-form so that the gas passed into the internal space of the pre-form exits the preform through the outlet.

According to a preferred embodiment, a second end section of the preform having an outlet of the preform is held by a second clamping device. Thus, this second gas flow builds up a counter pressure to the gas flow through the inlet on the first end section of the preform and allows controlling and reducing the flow rate as well as reducing the pressure and temperature gradient of the fluid within the preform.

Figure 3:
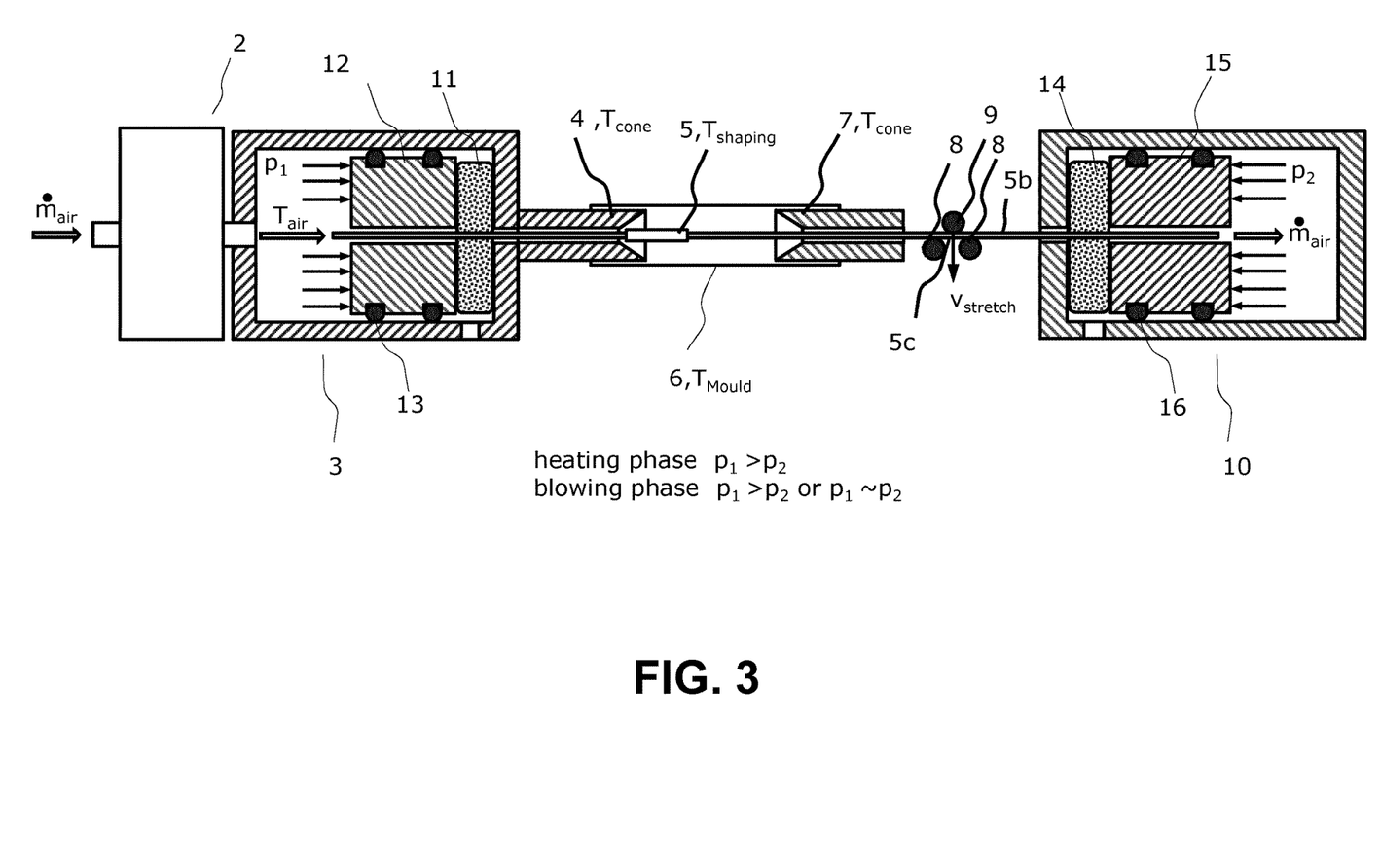
FIG. 3 shows an embodiment of the method/device according to the present invention.

According to yet another embodiment of the method according to the present invention, the first cone is integrated into the first clamping device, i.e. it forms a part of the first clamping device. A silicone ring inside the clamping device is compressed by a piston inside the clamping device. Thus, the silicone ring assures an airtight connection and also allows clamping the tubing inside the clamping device (FIG. 3).

Furthermore, according to an embodiment of the method according to the present invention, shaping the preform into a balloon includes applying a tension to the pre-heated preform to stretch the pre-form in the axial direction.

Preferably, the tension can be applied by exerting a suitable force onto the second end section of the preform. Preferably, this may be achieved by arranging/supporting the second end section of the preform that protrudes out of the second cone on two rolls and by applying a weight to a portion of the preform extending between the two rolls or by exerting a spring force onto the portion extending between the two rolls. The weight or spring force can than act perpendicular to the axial direction and is deflected by the rolls in the axial direction to cause the desired tension in the axial direction.

Furthermore, according to an embodiment, shaping the preform into a balloon includes passing gas into the internal space of the pre-heated preform via the first clamping device and via the inlet of the preform to apply a pressure in the internal space of the preform such that the pre-heated preform expands radially and axially until it contacts the tube and the cones to form the balloon.

Preferably, the heated gas or fluid can be passed through the internal space of the preform until the preform attains the shaping temperature. Then, if necessary, the pressure of the gas can be further increased to initiate the shaping of the balloon. I.e. the gas can comprise essentially the same temperature as during the pre-heating period but an increased pressure to start shaping of the balloon such that the pre-heated preform expands radially and axially until it contacts the tube and the cones. The step of applying a tension to the pre-heated perform before may also be omitted according to an embodiment and shaping the balloon may be conducted by merely supplying sufficient pressure of the gas or fluid passed into the preform via the inlet of the preform.

Further, in an embodiment, upon shaping the preform into a balloon by passing gas into the internal space of the pre-heated preform (to apply a pressure in the internal space of the preform such that the pre-heated preform expands radially and axially until it contacts the tube and the cones to form the balloon), the preform is closed at the second end section by the second clamping device so that the gas cannot exit the preform via the outlet.

Alternatively, the second end section/the outlet of the preform can also be open upon shaping the preform to a sufficient length in the axial direction so that a sufficient pressure can build up in the internal space of the preform.

Furthermore, according to an embodiment of the method according to the present invention, in order to locate a spot at which shaping of the preform starts on a section of the preform that is arranged in the tool, at least one of the following steps is conducted:
locally heating a region of the section,
mechanically stretching a region of the section,
adjusting the temperature of the tool (i.e. of the cones and of the tube) to a level above the ambient temperature so that the preform does not expand outside the tool, i.e. outside the form defined by the cones and the tube, heating the first cone to a set temperature below the melting point of the balloon material using a separate heater in order to soften that region of the preform that is inside the first cone, to a local temperature on the preform in order to reduce the pressure that is needed for initiating the radial expansion. Ideally the necessary opening pressure is below the pressure that is needed for the axial expansion to finish the balloon to gain control over the axial expansion ratio (i.e. extension of the radial expansion of the section of the preform in the axial direction towards the second cone); preferably, this means that the radial expansion/opening of the preform can be started and preferably also stopped in the first cone.

Preferably, the separate heating the first cone is performed continuously or before passing the (preferably heated) gas into the internal space of the pre-heated preform via the inlet for shaping the balloon. Depending on the cone material the heating can be via convection, electrically or induction.

Further according to an embodiment of the method according to the present invention the axial direction along which the preform extends upon pre-heating and/or shaping can extend horizontally as well as vertically. Other spatial orientations are also possible.

According to a further aspect of the present invention, a device for shaping a balloon, particularly a balloon of a balloon catheter, particularly a balloon catheter for performing an angioplasty, as suggested herein is disclosed, wherein the device includes:

- a tool for receiving a preform that is to be shaped into a balloon,
- at least a first clamping device for holding a first end section of the preform when the preform is arranged in the tool,
- at least a first heater configured to heat a gas or fluid that is to be passed into the preform for pre-heating the preform, wherein the first heater is in flow connection with the first clamping device such that a gas or fluid heated by the first heater can be passed into an internal space of the preform via an inlet of the preform at the first end section of the preform for pre-heating the preform when the first end section of the preform is held by the first clamping device.

Preferably, according to an embodiment of the device according to the present invention, the tool includes a tube extending in an axial direction, and a first and an opposing second cone facing each other in the axial direction, wherein, when the preform is arranged in the tool, the preform extends in the axial direction through the first cone, the tube and the second cone and is surrounded by the first cone, the tube and the second cone. Furthermore, in detail, the two cones and the tube can be formed as already described above regarding the method according to the present invention.

Furthermore, according to an embodiment of the device according to the present invention, the first cone is integrated into the first clamping device.

Further, according to an embodiment of the device according to the present invention, the first heater is a flow heater.

Further, preferably, as already described above, the first heater is preferably configured to control the temperature of the gas or fluid that is to be fed into the internal space of the preform so that the heated gas or fluid has a pre-definable temperature. The control can be a closed-loop control. Alternatively, also an open-loop control may be applied (see also above).

Furthermore, according to an embodiment of the device according to the present invention, the device includes a second clamping device configured to hold a second end section of the preform that protrudes out of the second cone when the preform is arranged in the tool. Preferably, the second clamping device is configured to comprise an open state so that gas or fluid passed into the preform via the inlet for pre-heating of the preform can exit the preform via an outlet at the second end section, and a closed state in which the second end section is blocked and gas or fluid passed into the internal space of the preform via the inlet for shaping the preform into a balloon cannot exit the internal space of the preform via the outlet.

Preferably, according to a preferred embodiment, the second clamping device is configured to hold a second end section of the preform that protrudes out of the second cone when the preform is arranged in the tool, wherein the device includes a second heater that is configured to heat a gas or fluid that is to passed into the preform for pre-heating the preform, wherein the second heater is in flow connection with the second clamping device such that a gas or fluid heated by the second heater can be passed into an internal space of the preform via an inlet of preform at the second end section of the preform for pre-heating the preform when the second end section is held by the second clamping device.

Preferably the second heater can be configured as already described above regarding the method according to the present invention.

Furthermore, according to an embodiment of the device according to the present invention, the device includes a tensioning device configured to apply a tension to the pre-heated preform to stretch the preform in the axial direction. Preferably, the tensioning device includes two rolls for supporting the second end section as well as a weight or a spring for exerting a force on a portion of the second end section that extends between the two rolls when the second end section is supported on these rolls. Due to the rolls, the force exerted onto the portion of the second end section by the weight or spring is deflected by the rolls in the axial direction to cause the desired tension.

Furthermore, according to an embodiment, the axial direction extends horizontally or vertically when the device is in an operational state.

Due to the invention, the device for forming a balloon includes a simplified design. The gas (e.g. pressurized air) is used for pre-forming as well as for shaping (e.g. blowing) the preform into a balloon. No movable tool parts are necessary (apart from a mechanism for applying a tension to the preform in the axial direction). Furthermore, a higher precision concerning tempering of the shaping temperature as well as faster temperature changes can be achieved.

Further, the invention drastically decreases the influence of the balloon tube cross section on the shaping temperature of the preform and guarantees a stable blowing temperature and therefore a more stable stretch blow molding process.

Furthermore, shorter cycle times due to the forced convection in the internal space of the preform reduce the heating-up time from 3 s to 20 s (depending on the preform cross section) below 1 s. Further, cycle times are significantly reduced due to the decoupling of blowing and tempering temperature: instead of 64 s at 140° C. the same tempering effect can be achieved in 8 s at 170° C.

Furthermore, due to the hot spot and the temperature wave travelling from the first clamping device/first cone to the second clamping device the stretch blow molding process can be decelerated and preferably allows to synchronize the axial shaping of the balloon and the axial stretching.

Figure 1:
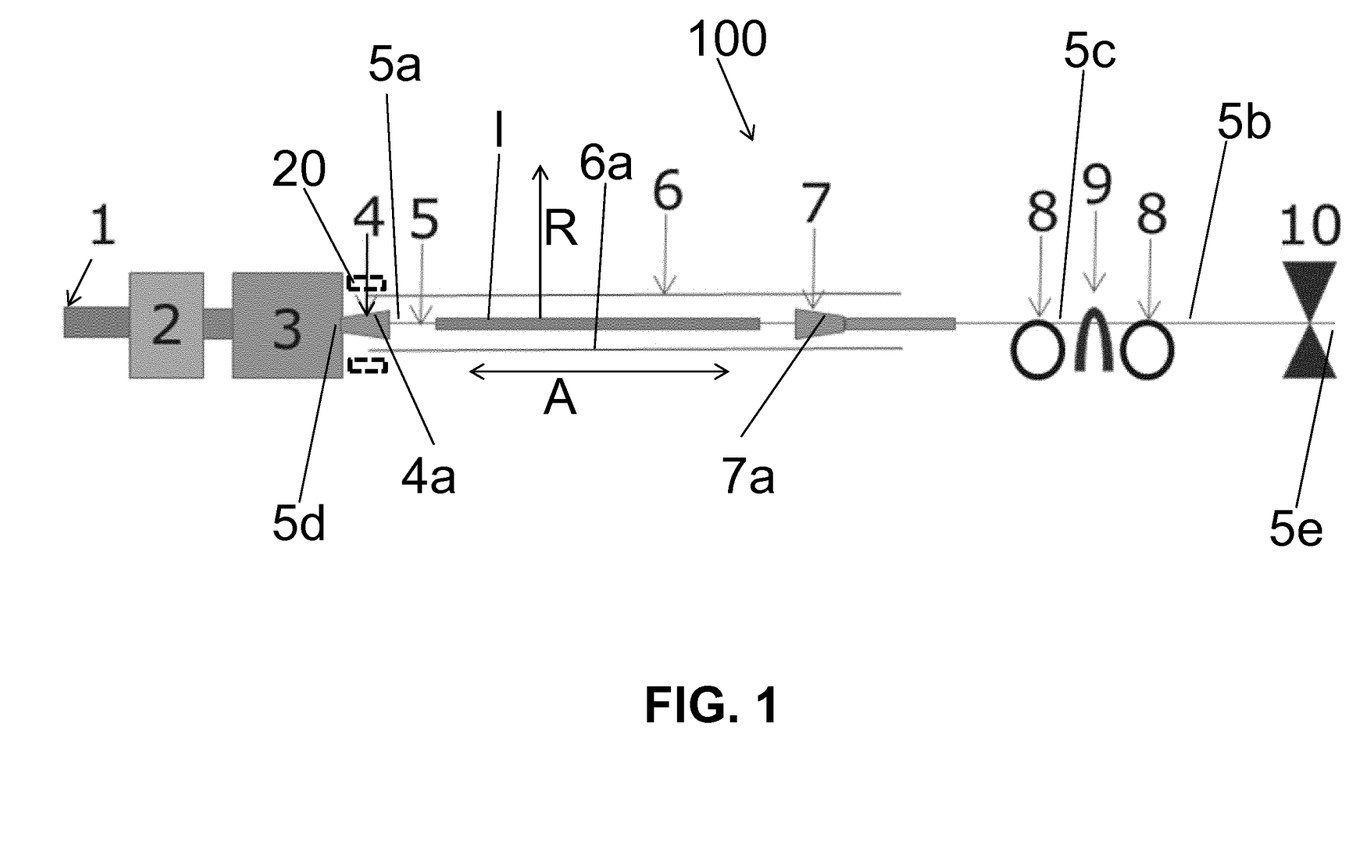
FIG. 1 shows an embodiment of the method/device according to the present invention.

FIG. 1 shows an embodiment of a device 100 for shaping a balloon according to the present invention, having a tool 6, 4, 7 for receiving a preform 5 in an internal space I of the tool, which preform 5 is to be shaped into a balloon. Preferably, the tool includes a first cone 4 and a second cone 7 as well as a tube extending in an axial direction A, such that the two cones face each other in an axial direction A and are both insertable into the tube 6 of the tool at opposing ends of the tube 6 so that the tapered insides 4a, 7a of the cones 4, 7 together with the inside 6a of the tube 6 delimit the internal space I which defines the form of the balloon to be shaped. Preferably, the insides 4a, 7a, 6 delimit the radial and axial shaping of the preform 5 upon blow molding the balloon.

When the preform 5, that is e.g. formed as an elongated balloon tube, is inserted in the internal space I, a first end section 5a protrudes out of the first cone 4 into a first clamping device 3 which is preferably integrally formed with the first cone 4. The first clamping device 3 is configured to clamp the first end section 5a so that a heated gas or fluid can be passed into the internal space I of the preform 5 via an inlet 5d of the preform 5 arranged at the second end section 5a of the preform 5. Preferably, the first clamping device 3 is configured to clamp the first end section 5a of the preform 5 so that a heated gas or fluid can be passed into the internal space I of the preform 5 via an inlet 5d of the preform 5.

The heated gas is preferably air which is heated by means of a first heater 2 upstream the first clamping device 3. Preferably, the device 100 includes an inlet 1 for the pressurized gas (e.g. air) upstream the first heater 2, so that the gas can be passed via the inlet 1, the first heater 2 and the clamping device 3 into the inlet 5d of the preform 5. The gas may comprise a pressure of up to 54 bar at the inlet 1 of the device 100. Further, the first heater 2 is configured to control the temperature of the gas. Preferably, the temperature of the gas is e.g. heated to 70° C. by the first heater 2.

Furthermore, a second end section 5b of the preform 5 having an outlet 5e of the preform 5 protrudes out of the second cone 7 and is passed via two rolls 8 to a second clamping device 10 which holds the second end section 5b of the preform 5. A weight 9 exerts a force onto a portion 5c of the preform 5, which portion 5c extends between the two rolls 8 in the axial direction A. Due to the rolls 8, the force generated by the weight 9 tensions the preform 5 in the axial direction A for stretching the pre-heated preform 5 (see also below).

Preferably, the second clamping device 10 is open when tempering the preform 5 with the heated gas or fluid so that the gas or fluid can leave the preform 5 at the outlet 5e of the preform 5. In case the second end section 5b of the preform includes a sufficient length, the balloon can also be formed by feeding gas or fluid into the inlet 5d of the preform due to a dynamic pressure building up in the internal space I of the preform 5.

Furthermore, by stretching or thermal pre-processing of the end sections 5a, 5b of the preform, the weakest part of the preform can be located in the internal space I of the tool 6, 4, 7 to force an opening (i.e. initial radial expansion) of the preform 5 within the internal space I. It is also possible to locally heat-up a section of the preform to generate a hot spot at which the balloon forming (radial expansion) will start.

It is also possible to maintain the tool's 6, 4, 7 temperature at a slightly increased level above the ambient temperature, so that the preform 5 does not widen outside the tool 6, 4, 7.

Preferably, the process of tempering/pre-heating the preform 5 by passing heated gas (e.g air) or fluid into the internal space I of the preform 5 takes place in the above-described phases. In case the preform tension surpasses the flow stress at a location of the preform, the preform spontaneously expands/opens radially and axially until the radial expansion is delimited by the inside 6a of the tube 6 (or one of the tapered insides 4a, 7a of the cones 4, 7). From there the preform 5 expands axially in the directions of the cones 4, 7 that delimit the axial lengths of the balloon to be formed.

Preferably, in case of a homogenous temperature distribution the pressure necessary for starting the radial expansion in the preform 5 to form a balloon generally lies above the pressure necessary for axially shaping/expanding the preform. These different pressure demands cause considerably short balloon shaping times, which lie in the range of a few milliseconds. Thus, synchronizing the stretching of the preform 5 (e.g. due to weight 9) in the axial direction A and expanding the preform 5 radially and axially can be difficult.

In case the axial shaping of the balloon outruns the stretching of the axial direction A axial expansion is reduced, and the wall thickness of the balloon locally increases.

However, forcing the shaping of the balloon to start at a certain section of the preform 5 allows to synchronize the axial balloon shaping and the stretching generated e.g. by means of the weight 9.

For this, the first cone 4 can be heated in a manner that the pressure needed for further axial expansion of the preform 5 lies above the pressure needed for initially expanding the preform 5 radially (initial opening/widening of the balloon). Then, the shaping of the preform 5/balloon can be started in the first cone 4 and may also be stopped there. Further, balloon expansion can then be controlled via purging of the heated gas (e.g. air) or fluid into the internal space I of the preform 5/balloon at a suitable pressure.

In case the pressure of the gas used to pre-heat the preform 5 is sufficiently high, the pressure drop at the second end section of the preform 5 is so high that a balloon can also be formed spontaneously when the second clamping device 10 is open and does not block the second end section 5b/outlet 5e of the preform 5.

The shaping method (e.g. stretch blow moulding) according to the present invention is particularly suitable for forming thermoplastic polymers (PA12, PA11, PEBA, PVC, TPU, PEEK, PET). Today, the majority of balloons used for PTA and PTCA are made of polyamide (PA) or polyether block amide (PEBA) Preferably, in such a process the preform can be stretched/expanded in the peripheral and in the longitudinal (i.e. axial) direction by 500% up to 700% (peripheral direction) and 220% up to 300% (axially). The balloon blowing process is a thermoforming procedure that biaxially aligns the polymer chains in the direction of the greatest stress encountered in balloon dilatation and is the reason for the massive increase in their burst strength.

Preferably, blow moulding can utilize the higher chain mobility of the macro molecules above the glass transition temperature. An increased temperature reduces the tension at which the macro molecules slide along one another and the preform can be plastically expanded. In the process, the mobility of the macro molecules increases and the macromolecules re-orient within the preform/balloon. This shaping of polyamide based materials occurs in a temperature range above the glass transition temperature of about 48° C. to 178° C.

When using a stretch blow molding process according to the present invention as indicated in FIG. 1 (two step process), the preform 5 is pre-heated/tempered in a first step in the tool 6, 4, 7 by passing heated gas (e.g. air) or fluid into the internal space I of the preform 5 to adjust the temperature of the preform to about 50° C. to 100° C. (particularly to just below the melting temperature). Pre-heating may comprise periods where no heating of the pre-form occurs so that a temperature equalisation can take place over the entire wall thickness of the preform 5.

Figure 2:
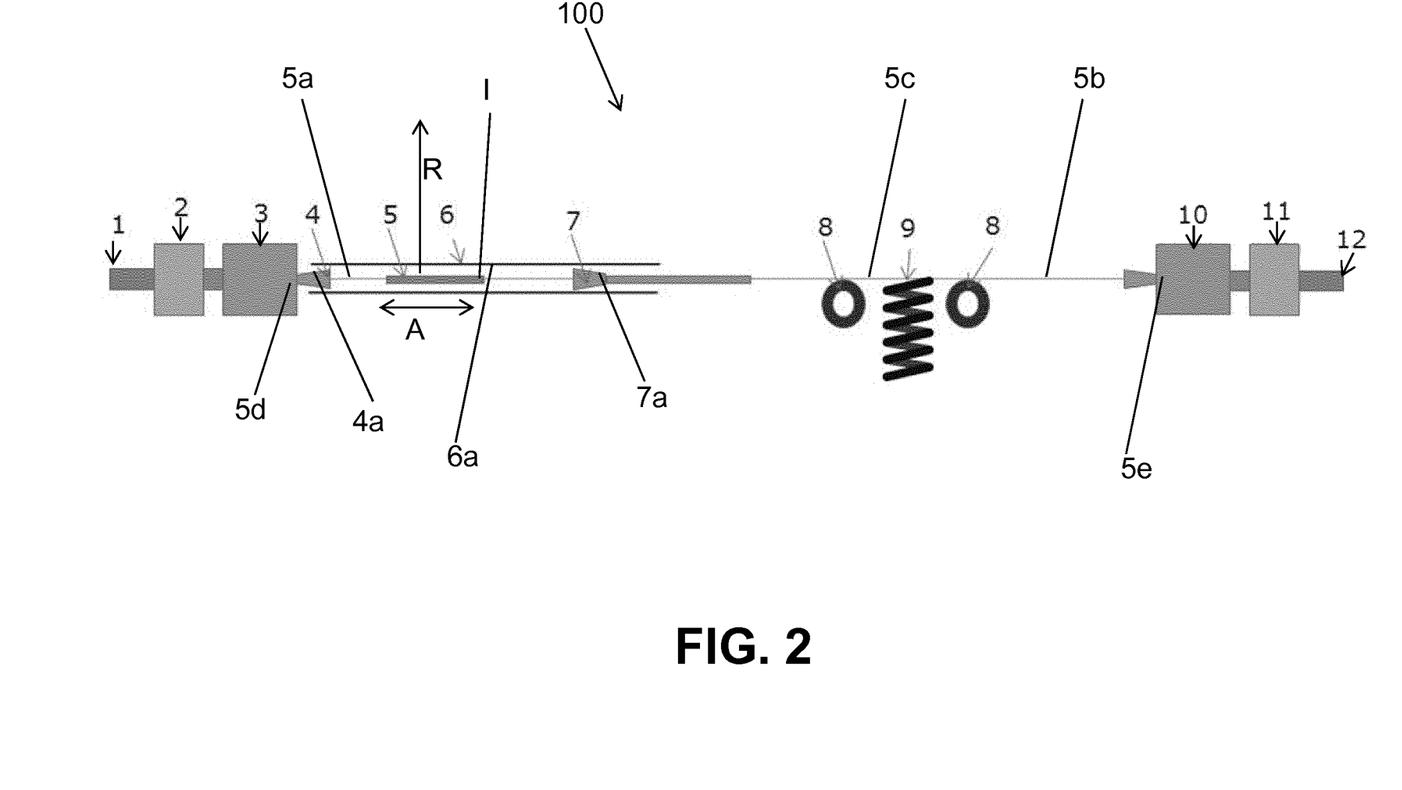
FIG. 2 shows a further embodiment of the method/device according to the present invention.

Once the pre-heating of the preform 5 is done, the preform is axially stretched mechanically (e.g. using the weight 9, a spring or a motor as schematically indicated in FIG. 2). Before, with the stretching or at a certain stretching gas is fed into the internal space of the preform to build up the pressure necessary to plastically expand the preform material axially and radially until it contacts the insides 4a, 7a, 6a of the cones 4, 7 and the tube so that the balloon receives its final shape. For this shaping of the balloon, pressures of the gas in the range from 7 bar to 50 bar can be used. The pressure required depends on the mechanical properties, thickness and temperature of the preform. After cooling of the tool and pressure relief, the tool 6, 4, 7 is opened and the balloon can be removed from the tool 6, 4, 7.

FIG. 2 shows a modification of the device 100 shown in FIG. 1. Here, the second end section 5b is held by a second clamping device 10 that is in flow connection with a second heater 11 so that gas can also be passed into an outlet 5e of the preform 5 at the second end section to generate a counter pressure. This allows reducing the flow rate of the gas flows entering the preform in inlet 5d.

Furthermore, in both embodiments shown in FIGS. 1 and 2, the first cone 4 may be heated separately in order to force initial radial balloon expansion in to occur in the first cone 4. For this, a separate heater 20 (e.g. an inductor) may be used. Here, the electromagnetic waves generated by the inductor do not affect the glass tube 6 but merely heat the metal first cone 4. According to an example of the present invention, the temperature of the first cone 4 can be increased to 120° C. in 7.5 s. The first cone 4 may also be heated permanently in order to keep the cycle times short.

Furthermore, it is possible to arrange the device 100 such that the axial direction A extends horizontally or even vertically.

Further in FIG. 3, the device for performing the method as suggested herein is shown in further detail. It is shown that a gas, here it is supposed to be air, having a first pressure p1 and a first temperature $T_{air}$, after having passed the first heater 2, is further passed through the first clamping device 3 into a preform. Thereby, the first cone 4 is integrated into the first clamping device 3, i.e. it forms a part of the first clamping device. A first air tight seal 11, e.g. in form of a silicone ring inside the clamping device 3 is compressed by a pressing tool 12, e.g. in form of a piston, having seals 13 inside the clamping device 3. Thus, first air tight seal 11 assures an airtight connection and also allows clamping the tubing inside the clamping device 3. Corresponding assembly is integrated into second clamping device 10, having a second air tight seal 14, e.g. in the form of a soft silicone ring, a second pressing tool 15 with seals 16.

REFERENCE SIGNS device 100
inlet 1
first heater 2
first clamping device 3
first cone 4, tapered insides 4a
preform 5
internal space I
first end section 5a
second end section 5b,
portion 5c, inlet 5d, outlet 5e
tube 6, inside 6a of the tube
second cone 7, tapered insides 7a
rolls 8
weight 9
second clamping device 10
first air tight seal 11
first pressing tool 12
seals 13
second air tight seal 14
second pressing tool 15
seals 16
separate heater 20

The invention claimed is:

1. A method for forming a balloon comprising the steps of:
providing a preform having a circumferential wall that encloses an internal space, pre-heating the preform while it is held in an open state by passing a heated gas or fluid through the preform via an inlet of the preform into the internal space and out of an outlet of the preform, wherein the preheating is conducted to raise a temperature of the preform to a temperature just below the melting temperature for a period to allow temperature equalisation over an entire wall thickness of the preform, and shaping the pre-heated preform into a balloon by increasing the pressure of the heated gas or fluid in the preform while maintaining an essentially same temperature of the heated gas or fluid from the pre-heating.

2. The method according to claim 1, wherein the step of providing comprises providing a tool comprising a tube extending in an axial direction, a first cone and an opposing second cone facing each other in the axial direction, and arranging the preform in the tool such that the preform extends in the axial direction through the first cone, the tube and the second cone, and is surrounded by the first cone, the tube and the second cone.

3. The method according to claim 2, wherein a first end section of the preform comprising the inlet is held by a first clamping device such that said heated gas or fluid can be passed into the preform via said inlet.

4. The method according to claim 3, comprising heating the gas or fluid outside of the tool in a first heater that is upstream of the first clamping device.

5. The method according to claim 3, wherein a second end section of the preform protrudes out of the second cone and includes the outlet of the perform, and is held by a second clamping device in an open state during the pre-heating of the preform so that the gas or fluid passed into the internal space of the preform exits the preform through the outlet.

6. The method according to claim 3, wherein a second end section of the preform comprising the outlet of the preform is held by a second clamping device and the heated gas or fluid flow from the preform is reduced by a counter pressure applied in outlet.

7. A method for forming a balloon comprising the steps of: providing a preform having a circumferential wall that encloses an internal space, pre-heating the preform while it is held in an open state to a shaping temperature by passing a heated gas or fluid through the preform via an inlet of the preform into the internal space and out of an outlet of the preform, and shaping the pre-heated preform into a balloon, wherein the shaping comprises reducing flow of the gas or fluid by applying a counter pressure to the end of the preform via the outlet.

8. The method according to claim 3, wherein the first cone is integrated into the first clamping device.

9. The method according to claim 1, wherein the shaping comprises applying a tension to the preform to stretch the preform in the axial direction.

10. The method according to claim 5, comprising closing the second end section with the second clamping device during the shaping so that said gas or fluid cannot exit the preform via the outlet.

11. The method according to claim 2, wherein the axial direction extends horizontally or vertically.

12. The method according to claim 1, wherein the step of shaping comprises holding the preform in the open state and passing gas through the preform at a pressure sufficient to shape the preform into a balloon.

13. The method according to claim 1, wherein the step of shaping comprises closing the outlet of the preform and passing gas into the preform into the internal space.

14. The method according to claim 1, wherein the step of shaping is conducted above a glass transition temperature of the preform.

15. The method according to 7, wherein the counter pressure is created by heated gas or fluid passed into the internal space of the preform via the outlet.

16. A method for forming a balloon comprising the steps of:
providing a preform having a circumferential wall that encloses an internal space, pre-heating the preform to a shaping temperature by passing a heated gas or fluid via an inlet of the preform into the internal space, and shaping the pre-heated preform into a balloon, wherein the step of providing comprises providing a tool comprising a tube extending in an axial direction, a first cone and an opposing second cone facing each other in the axial direction, and arranging the preform in the tool such that the preform extends in the axial direction through the first cone, the tube and the second cone, and is surrounded by the first cone, the tube and the second cone, and creating a spot at which shaping of the preform starts on a section of the preform that is arranged in the tool, wherein the creating comprises:
mechanically stretching a region of the section,
locally heating a region of the section,
adjusting the temperature of the tool to a level below the melt temperature of the balloon material,
heating the first cone using a separate heater in order to heat the section to a temperature at which an expansion pressure in the internal space of the preform leads to a radial expansion of the section towards a tapered inside of the first cone, wherein the expansion pressure is smaller than a pressure that would cause further axial expansion of the preform.

17. A device for shaping a balloon, comprising:
a tool configured to receive a preform that is to be shaped into a balloon, the tool having a first cone, a second cone, and a tube extending in an axial direction between the first and second cones that face each other in the axial direction and are both insertable into the tube at opposing ends of the tube so that tapered insides of the first and second cones together with an inside of the tube delimit an internal space without moving parts during preheating and shaping, the internal space without moving parts defining the form of the balloon to be shaped,
at least a first clamping device to hold a first end section of the preform when the preform is arranged in the tool,
at least a first heater configured to heat a gas or a fluid, wherein the first heater is in fluid connection with the first clamping device such that a gas or fluid heated by the first heater can be passed into an internal space of the preform via an inlet of the preform at the first end section of the preform for pre-heating the preform when the first end section is held by the first clamping device and that the gas or fluid can be passed in the internal space of the preform to form the balloon formed with the internal space without moving parts.

18. A method for forming a balloon comprising the steps of:
providing a preform having a circumferential wall that encloses an internal space, pre-heating the preform while it is held in an open state to a shaping temperature by passing a heated gas or fluid through the preform via an inlet of the preform into the internal space and out of an outlet of the preform until the preform attains the shaping temperature, and shaping the pre-heated preform into a balloon by passing a heated gas or fluid into the internal space of the pre-heated preform to apply a pressure in the internal space of the preform such that the preform expands radially and axially.

19. A method for forming a balloon comprising the steps of:
providing a preform having a circumferential wall that encloses an internal space, pre-heating the preform while it is held in an open state to a shaping temperature by passing a heated gas or fluid through the preform via an inlet of the preform into the internal space and out of an outlet of the preform until the preform attains the shaping temperature;
after the preform attains the shaping temperature, mechanically axially stretching the preform; and
shaping the pre-heated preform into a balloon by passing a heated gas or fluid into the internal space of the pre-heated preform to apply a pressure in the range of 7 bar to 50 bar in the internal space of the preform such that the preform expands radially and axially.

20. A method for forming a balloon comprising the steps of:
providing a perform having a circumferential wall that encloses an internal space, pre-heating the preform while it is held in an open state to a shaping temperature by passing a heated gas or fluid through the preform via and inlet of the preform into the internal space and out of an outlet of the preform, and shaping the pre-heated preform into a balloon, wherein the pre-heating is conducted in three phases that may overlap each other and comprise an axial phase, a radial phase and final phase, wherein
in the axial phase, the heated gas or fluid travels as an axial heating wave through the initially cold preform and gradually cools down by transferring heat to the inner surface of the preform;
in the radial phase, when an inner surface temperature of the approaches a temperature of the heated gas or fluid, heat transfer from the heated gas or fluid to the inner preform surface drops and an axial temperature profile of the preform is substantially homogenous, whereby a second temperature wave travels in the radial direction through the preform due to heat conduction; and in the final phase, a final pre-heat temperature profile of the preform is established due to radiant heat exchange and thermal conduction with its surroundings.

\* \* \* \* \*